United States Patent [19]

Richardson et al.

[11] Patent Number: 5,490,980
[45] Date of Patent: Feb. 13, 1996

[54] COVALENT BONDING OF ACTIVE AGENTS TO SKIN, HAIR OR NAILS

[75] Inventors: Norman K. Richardson, Rockaway, N.J.; Kurt M. Schilling, Parkgate, England; David J. Pocalyko, Lincoln Park, N.J.; Peter L. Bailey, Heswall, Great Britain

[73] Assignee: Chesebrough-Pond's USA Co., Division of Conopco, Inc., Greenwich, Conn.

[21] Appl. No.: 314,178

[22] Filed: Sep. 28, 1994

[51] Int. Cl.$^6$ .......................... A61K 38/46; A61K 37/00
[52] U.S. Cl. ................................. 424/94.6; 514/2
[58] Field of Search ................. 514/2; 424/94.6

[56] References Cited

FOREIGN PATENT DOCUMENTS

| 0615745 | 9/1994 | European Pat. Off. . |
| 1-173275 | 2/1991 | Japan . |

OTHER PUBLICATIONS

Derwent Abstract of JP 3213574. (1991).
Derwent Abstract of JP 3095109. (1991).
Derwent Abstract of JP 3083908. (1991).
Derwent Abstract of JP 3038511. (1991).
Derwent Abstract of JP 2204407. (1990).
Derwent Abstract of JP 2169511. (1990).
Dutton, A. et al., "Crosslinking and Labeling of Membrane Proteins by Transglutaminase-catalyzed Reactions" *Proc. Nat. Acad. Sci. USA*, vol. 72, No. 7, Jul. 1975, pp. 2568–2571.

*Primary Examiner*—Zohreh Fay
*Attorney, Agent, or Firm*—Rimma Mitelman

[57] ABSTRACT

Transglutaminase crosslinks proteins by catalyzing the formation of isopeptide bonds between lysine and glutamine residues. Transglutaminase may be used to crosslink beneficial actives containing an amine moiety to glutamine residues in skin, hair or nails. A variety of beneficial actives, e.g., sunscreens, antimicrobial compounds, skin conditioning agents, hair conditioning agents, anti-inflammatory compounds, antioxidants, coloring agents, perfumes, insect repellants, can thus be delivered to human skin, hair, or nails.

9 Claims, No Drawings

COVALENT BONDING OF ACTIVE AGENTS TO SKIN, HAIR OR NAILS

FIELD OF THE INVENTION

The invention relates to compositions for topical application to human skin, hair, or nails, which compositions contain transglutaminase and a beneficial active ingredient containing, or so modified as to contain, an alkylamine group.

BACKGROUND OF THE INVENTION

Transglutaminase is a calcium and thiol dependent enzyme which is found in a number of organs and tissues (epidermis, hair follicles, liver, blood, etc.) and which is responsible for the crosslinking of proteins by the formation of covalent bonds between lysine and glutamine residues. Transglutaminase has a high specificity for protein-bound glutamine residues and a low specificity for lysine. A variety of amines have been reported as substrates for transglutaminase, including dansylcadaverine, methyl amine, butyl amine, histamine and putrescine and hydroxylamine. Hydroxylamine is in fact the amine donor in a standard assay for transglutaminase activity wherein hydroxylamine is covalently bound to an N-terminal blocked peptide containing glutamine and glycine to produce hydroxamate, which is detected by color formation in the presence of ferric chloride and acid. One Unit of transglutaminase is defined as that amount which will form 1 µMole of hydroxamate per minute at 37° C.

It is also known that the fluorescent primary amine dansylcadaverine can be introduced to a variety of protein substrates via transglutaminase. These include fibrin, casein and B-lactoglobulin, cold insoluble globulin, alpha$_2$-macroglobulin, erythrocyte ghosts and proteins in sarcoplasmic reticulum, myosin and actin, rhodopsin, and guinea pig liver transglutaminase itself.

Lorand et al., "The specificity of guinea pig liver transglutaminase for amine substrates," Biochem. 18, 1756–1765 (1979), discloses the specificity of guinea pig liver transglutaminase for synthetic primary amines having high apparent affinities for transglutaminase. These studies revealed that optimal transglutaminase activity was achieved when compounds had (a) alkylamine side-chain lengths equivalent to 5 methylene groups (or 7.2–7.6 Å long), (b) no branching nor groups bulkier than methylene along the alkyl amine chain and (c) hydrophobic moieties attached to the alkyl chain.

Japanese patent application 3213574 discloses the use of transglutaminase to cross-link the amino acid functional groups of the cuticle part of the animal hair in order to produce hair or hair fiber containing materials having good shrinkage resistance, pill resistance, and hydrophobic property. Japanese patent application 3095109 and Japanese patent application 3083908 disclose hair or skin cosmetic material containing transglutaminase modified with a water-soluble substance, e.g., polyethyleneglycol, ethyleneglycol, propyleneglycol, glycerine, PVA, glucose, sucrose, fructose, alginic acid, CMC, starch and hydroxypropylcellulose. Japanese patent application 3038511 discloses cosmetic compositions containing transglutaminase. The compositions are said to give a good conditioning effect. Japanese patent applications 2204407 and Japanese patent application 2169511 disclose hair and skin cosmetic materials containing transglutaminase and water-soluble polyhydride alcohol and optionally calcium salt. The Japanese patent applications disclose the repair of damaged skin or hair surfaces by the action of transglutaminase upon cuticle or stratum corneum. Transglutaminase itself is the active ingredient in the disclosed compositions. None of the above-referenced Japanese patent applications describe the use of transglutaminase in conjunction with an active agent containing an alkylamine moiety.

It is an object of the present invention to provide a composition for delivery of an active ingredient to human skin, hair, or nails.

It is another object of the present invention to provide a composition for topical application to human skin, hair, or nails, which composition contains transglutaminase and an active ingredient including an alkylamine moiety.

These and other objects of the invention will become more apparent from the detailed description and examples that follow.

SUMMARY OF THE INVENTION

The above objects are attained by the present invention which includes a composition for topical application to human skin, hair, or nails, the composition containing:

a) an effective amount of at least one active ingredient which includes or is modified to include at least one —R'NH$_2$ group wherein R' is a straight aliphatic hydrocarbon chain containing from 1 to 8 carbon atoms, preferably containing at least 5 carbon atoms;

b) transglutaminase in an amount effective to catalyze the covalent bonding of the active ingredient to glutamine residues in human skin, hair, or nails; and c) a pharmaceutically acceptable carrier in an amount effective to deliver transglutaminase and the skin benefit ingredient to human skin, hair, or nails.

DETAILED DESCRIPTION OF THE INVENTION

The first essential ingredient of compositions according to the present invention is an active ingredient which inherently includes or is modified to include at least one —R'NH$_2$ moiety wherein R' is a straight aliphatic hydrocarbon chain containing from 1 to 8 carbon atoms. Transglutaminase crosslinks the active ingredient, through the alkylamine (R'NH$_2$) moiety of the active, to the glutamine residues in skin, hair, or nails. Preferably, in order to optimize the crosslinking of the active ingredient by transglutaminase, the R'NH$_2$ moiety contains at least 5 unbranched carbon atoms adjacent to NH$_2$ group. Most preferably, the active ingredient included in the inventive compositions contains more than one alkylamine moiety, in order to attain enhanced binding of the active ingredient to transglutaminase.

The active ingredient suitable for inclusion in the inventive compositions may be any compound, the delivery of which to human skin, hair or nails, has a beneficial effect, as long as the compound contains, or is modified to contain, an alkylamine moiety. Suitable active ingredients include but are not limited to antimicrobial compounds, UV-absorbing compounds, skin conditioning agents, hair conditioning agents, anti-inflammatory compounds, antioxidants, coloring agents, perfumes, insect repellants, and mixtures thereof.

Suitable active ingredients which inherently contain an alkylamine moiety include but are not limited to skin and hair conditioning agents. Examples of suitable agents include but are not limited to intact proteins, hydrolyzed proteins, modified hydrolyzates, e.g., hydrolyzed collagen, keratin, elastin, hemoglobin, silk, rice, soy, wheat protein, corn, fibronectin, reticulin, serum protein, wheat gluten, peptides, and peptide derivatives. Suitable examples of active ingredient include but are not limited to to the materials summarized in the following table:

| SUPPLIER | TRADENAMES | TYPE OF MATERIAL |
| --- | --- | --- |
| Croda Chemicals Ltd. | Aminofoam C ™ | The triethanolamine salt of coconut fatty acid derivative of collagen amino acids plus low molecular weight collagen peptides. |
| Croda Chemicals Ltd. | Silk Protein Complex | Broad spectrum of silk "protein" molecular weight pieces including individual silk amino acids, short chain peptides and polypeptides with molecular weights up to as high as 50,000. |
| Croda Chemicals Ltd. | Hydrosilk 10,000 | Water soluble hydrolyzed silk protein with a molecular weight of approximately 10,000. |
| Croda Chemicals Ltd. | Crotein HKP S/F | Keratin hydrolozate. |
| Croda Chemicals Ltd. | Reficusol | Water soluble form of reticulin (MW of about 3,000). |
| Croda Chemicals Ltd. | Crolastin Series | Partially hydrolyzed elastine hydrogenation of non-lauric oil or hydrogenation of palm oil or at least partial hydrogenation. |
| Crodo Chemicals Ltd. | Byco C, A, O, E | Hydrolyzed collagen. |
| Brooks Industries, Inc. | Foam-Coll 4C, 4CT, 5 | Coco-hydrolyzed animal protein. |
| Brooks Industries, Inc. | Hydrocoll Series (many) | Hydrolyzed animal protein. |
| Brooks Industries, Inc. | Solu-coll Series (many) | Soluble animal protein. |
| Brooks Industries, Inc. | Quat-Coll QS | Steartrimonium hydrolyzed animal protein. |
| Brooks Industries, Inc. | Collamino 25, Complex | Collagen amino acids. |
| Brooks Industries, Inc. | Foam Soy C | Hydrolyzed soy protein and a stripped coconut fatty acid. |

| COMPANY | TRADENAMES | TYPE OF MATERIAL |
| --- | --- | --- |
| Brooks Industries, Inc. | Solu-soy EN-75 | Hydrolyzed soya bean protein, molecular weight of 1,000. |
| Inolex Corporation Personal Care Division | Lexein X250, X350, LP170 | Hydrolyzed animal protein. |
| Inolex Corporation Personal Care Division | Lexein X300, LP700 | Hydrolyzed animal protein. |
| Inolex Corporation Personal Care Division | Lexein CP125 | Cationic amido amine-protein salt. |
| Inolex Corporation Personal Care Division | Secol BA1 | Water soluble collagen. |
| Inolex Corporation Personal Care Division | Lexein A200, A210, A220, A240, S620 | Protein/fatty acid derivatives. |
| Inolex Corporation Personal Care Division | Lexein P50 | Collagen polypeptides (MW = 8,000). |
| Inolex Corporation Personal Care Division | Lexein A510 | Abietic Acid/hydrolyzed collagen derivatives. |
| Grunau GmbH | Lamepon S, S-TR, ST 40, S2, S2-TR | Condensation products of protein hydrolyzates with coconut fatty acids. |
| Grunau GmbH | Lamepon PA-TR | TEA-abietoyl hydrolyzed animal protein. |
| Grunau GmbH | Nutrilan 1, L, H | Hydrolyzed animal collagen. |
| Seiwa Kasei Co. Ltd. | Promois ™ series (many) | Hydrolyzed collagens; fatty acid derivatives; cationic polypeptides. |
| Hormel | Peptine 2000, PF-6, Sollagen, Sollagen "Extra Clear", Polypro 5000 | Hydrolyzed Animal Protein. |

The compounds discussed above contain an alkyl amine moiety. However, any compound having a beneficial effect on human skin, hair, or nails may be included in the inventive compositions as long as the compound is modified to contain at least one alkyl amine moiety.

The modified actives suitable for use in the present invention may be represented by general Formula I:

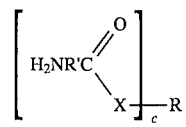

wherein $R'$ is $(CH_2)_a(CHNH_2)_b$ $X$ is oxygen, nitrogen, or sulphur,

R, the active ingredient part of a modified active, is selected from the group consisting of antimicrobial compounds, UV-absorbing compounds, skin conditioning agents, hair conditioning agents, anti-inflammatory compounds, antioxidants, coloring agents, perfumes, insect repellants, and mixtures thereof;

a is an integer from 5 to 12;

b is a number from 0 to 30, and c is a number from 1 to 4.

Examples of suitable antimicrobials which can be modified include but are not limited to phenol, cresol, hydroxybenzoates, triclosan, and salicylanilide, which are represented by formulae 1–5, respectively.

Modified Phenol — FORMULA 1

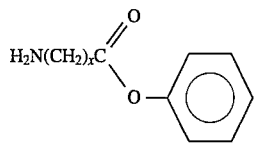

Modified Cresol — FORMULA 2

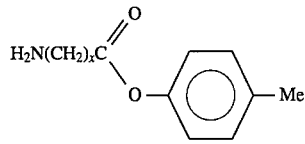

Modified Hydroxybenzoates — FORMULA 3

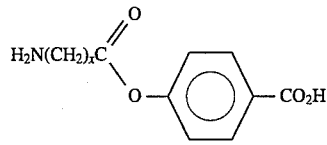

Modified Triclosan — FORMULA 4

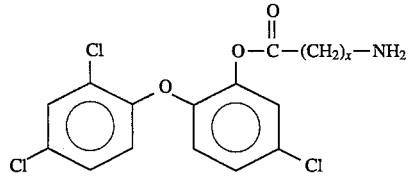

Modified Salicylanilide — FORMULA 5

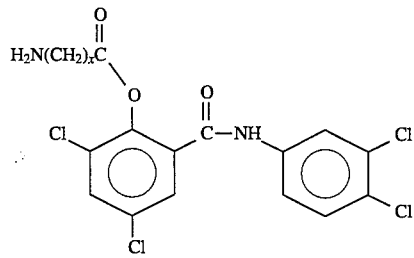

Examples of suitable modified UV-absorbing materials which can be modified include but are not limited to benzoates, oxybenzones, and cinnamic acid, which are represented by Formulae 6–8 respectively.

Modified Benzoates — FORMULA 6

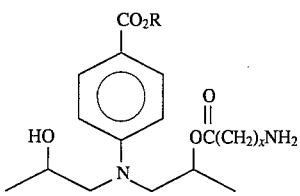

Modified Oxybenzone — FORMULA 7

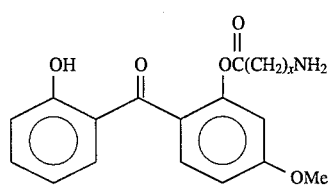

Modified Cinnamic Acid — FORMULA 8

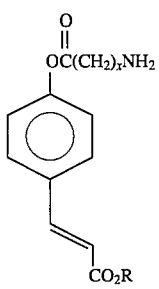

Examples of suitable skin conditioners and moisturizers which can be modified, include but are not limited to alpha-hydroxy acids, polyols, and hyaluronic acid, which are represented by Formulae 9–11 respectively.

Modified α-hydroxy acid — FORMULA 9

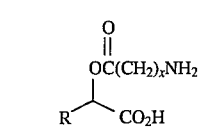

Modified Polyol — FORMULA 10

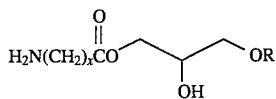

Modified Hyaluronic Acid — FORMULA 11

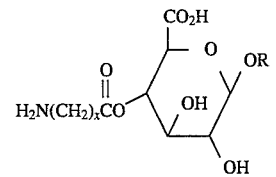

Examples of suitable anti-inflammatory agents which can be modified include but are not limited to corticosteroids or salicylates, which are represented by Formula 12 and 13, respectively.

Modified Corticosteroid                FORMULA 12

$$-OC(CH_2)_xNH_2$$ (attached to corticosteroid skeleton with =O, CH_3, HO, CH_3, and ketone)

Modified Salicylates                   FORMULA 13

$H_2N(CH_2)_xCO-$ on benzene ring with $-C(=O)OCH_3$

Examples of suitable antioxidants which can be modified include but are not limited to ascorbates and gallates, which are represented by Formula 14 and 15, respectively.

Modified Ascorbates                    FORMULA 14

$H_2N(CH_2)_xC(=O)-O-CH_2-CH(OH)-$ [ascorbate ring with OH, OH, =O]

Modified Gallates                      FORMULA 15

$H_2N-(CH_2)_x-C(=O)O-$ on benzene ring with HO, HO, and $CO_2R$

Examples of suitable hair conditioners which can be modified include but are not limited to proteins, amino acids, hydroxylated fats, and glycinates, which are represented by Formulae 16 and 17, respectively.

Modified Proteins, Amino Acids, and    FORMULA 16
Hydroxylate Fats $$R-OC(CH_2)_xNH_2$$
$$\parallel$$
$$O$$

Modified Glycinates                    FORMULA 17

$$R-\underset{\underset{CH_2CH_2OH}{|}}{\overset{\overset{CH_2CH_2OC(=O)(CH_2)_xNH_2}{|}}{C}}CH_2CO_2H$$

Examples of coloring agents which can be modified include but are not limited to phenol, naphthols, and hydroxy azo derivatives, which are represented by Formulae 18 and 19, respectively.

Modified Phenols and Naphthols         FORMULA 18

R-substituted benzene with $-OC(=O)(CH_2)_xNH_2$

Modified Hydroxy Azo Derivatives       FORMULA 19

$H_2N(CH_2)_x-CO-$ on naphthalene with R, linked via N=N to R-substituted phenyl Examples of suitable fragrances that can be modified include but are not limited to phenols such as menthyl salicylate, thymol, and vanillin, which are represented by Formulae 20–22 respectively.

Modified Thymol                        FORMULA 20

Benzene with CH_3, isopropyl, and $-OC(=O)(CH_2)_xNH_2$

Modified Vanillin                      FORMULA 21

Benzene with $-CHO$, $OCH_3$, and $-OC(=O)(CH_2)_xNH_2$

Modified Menthyl Salicylate            FORMULA 22

Menthyl (CH_3, isopropyl cyclohexyl) ester of salicylate with $-OC(=O)(CH_2)_xNH_2$ The synthesis of compounds 1–22 can be accomplished using a three-step reaction sequence similar to the Merrifield synthesis for peptides. The synthetic scheme involves 1) selectively blocking the amino group, 2) acylating the active using the blocked amino acid, and 3) selectively de-blocking the amine while leaving the newly formed ester bond intact. A more detailed description of each step is given below.

Reaction 1: Blocking the Amine

The selective blocking of amino functionalities of amino acid can be done by a variety of methods. The most widely used methods involve the formation of a carbamate. Any suitable selective blocking method can be used. A suitable blocking group is defined as one in which the blocking reaction can be done in a solvent for the amino acid, and the de-blocking reaction does not hydrolyze the ester bond formed in Reaction 2. Two examples of suitable blocking groups are given in Scheme I.

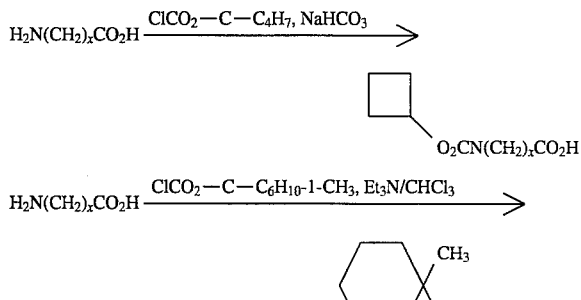

Reaction 2: Acylation of the Active

The second reaction in the synthesis of compounds 1–22 involves the acylation of the active, For compounds 1–22, this involves the formation of an ester bond, although the procedure described here can be used for the synthesis of amides as well. Typically, the reactivity of a carboxylic acid must be enhanced in order to achieve the acylated product in good yield. There are a number of effective acylating reagents which can be used with amino acids. One of the most widely used reagents which converts carboxylic acids directly to reactive acylating agents is dicyclohexylcarbodiimide (DCC) (Scheme II).

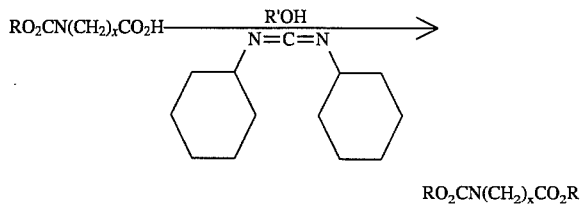

The acyl group of DCC coupled compounds is highly reactive because the cleavage of the acyl-oxygen bond converts the carbon-nitrogen double bond of the isourea to a more stable carbon-oxygen double bond. Because of their high reactivity, DCC activated compounds are not specific acylation reagents. Consequently, the site of acylation on the active will vary if there is more than one nucleophilic group. For compounds 1–22 the only potential nucleophiles are hydroxyls. In cases where there are more than one hydroxyl on the active (compounds 6, 7, 10, 11, 12, 14, and 15) it is likely that there will be more than one site of acylation.

The relative amount of acylation for a particular hydroxyl will be dependent on the nucleophilicity of group. Typically, primary hydroxyls will be acylated to a greater extent than secondary hydroxyls since they are more nucleophilic. Similarly, non-aromatic hydroxyls will be acylated to a greater extent than aromatic hydroxyls, since the π system of the aromatic ring de-localizes the negative charge of the hydroxylate thereby reducing its nucleophilicity.

Other suitable reagents used in activating carboxylic acids for acylation are imidazolides, isoxazolium salts, 2,2'-dipyridyl disulfide and triphenylphosphine, and 2-pyridyl thiochloroformate. There are other activating reagents which form reactive acyl halides. These methods may be appropriate in some cases but often use conditions which are more harsh than the methods listed above.

Reaction 3: De-protection of the Amine

The method for de-protecting the amine depends on the protecting group. The de-protection of most carbamates typically takes place under acid conditions. The synthesis of compounds 1–22 requires that the de-protection of the amine not cleave the ester bond formed in Reaction 2. There are a number of protecting groups for amines which can be removed selectively in the presence of an ester. The two groups listed in Scheme III are examples of such protecting groups.

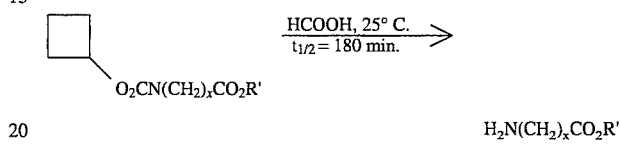

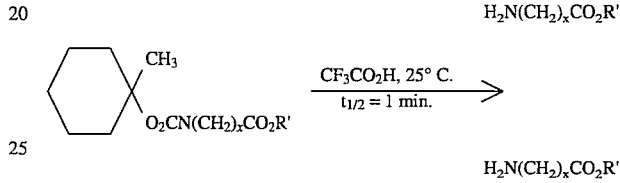

A general method for the synthesis of compounds 1–22 is shown Scheme IV.

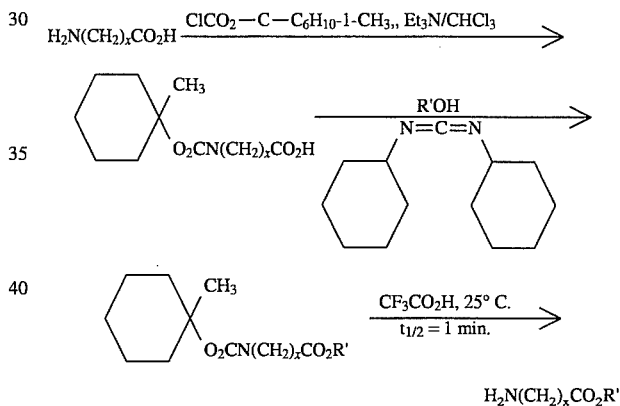

The active or modified active is included in the inventive compositions in an amount effective to deliver a benefit to skin, hair, or nails. The amount depends on the particular active employed. The amount of an active or modified active in the inventive compositions is typically in the range of from 0.0001% to 70% by weight of the composition, preferably in the range of from 0.1% to 5%.

The second essential ingredient in the compositions according to the present invention is transglutaminase. According to the present invention, transglutaminase acts as a catalyst to crosslink the active ingredient containing an alkylamine moiety with glutamine residues in skin, hair, or nails.

Sources of transglutaminase include: guinea pig liver, slime mold (*Physarum polycephalum*), alfalfa (*Medicago sativa*), and bacteria (*Bacillus subtilus*, Streptoverticillum sp.) Recently Ajinomoto Inc. patented a method for the production of inexpensive, food-grade transglutaminase by a batch fermentation process using bacteria containing genes from Streptoverticillum sp. Any transglutaminase is suitable for use in the present invention. Preferably, transglutaminase is obtained from Ajinomoto Inc.

Transglutaminase is employed in the inventive compositions in an amount effective to crosslink the active ingredient to glutamine residues in human skin, hair, or nails. Typically, transglutaminase is employed in catalytic amounts, generally in a range of from 0.001% to 20%, preferably in the range of from 0.01% to 5% by weight of the composition, and based on transglutaminase activity of 1.5–3.0 Units per mg of protein.

The composition according to the invention also includes a pharmaceutically acceptable vehicle to act as a diluant, dispersant or carrier for the active and transglutaminase in the composition, so as to facilitate the distribution of the active and transglutaminase when the composition is applied to the skin and/or hair and/or nails.

Vehicles other than water can include liquid or solid emollients, solvents, humectants, thickeners and powders. Examples of each of these types of vehicle, which can be used singly or as mixture of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoro ethane, propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica, sodium polyacrylate, tetra alkyl and/or trialkyl aryl ammonium smectites, chemically modified magnesium aluminium silicate, organically modified montmorillonite clay, hydrated, aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the composition and can, in the absence of other cosmetic adjuncts, form the balance of the composition.

The composition according to the invention may include optional skin benefit materials and cosmetic adjuncts, as long as the skin benefit material or the adjunct does not substantially reduce or eliminate the activity of transglutaminase or the active.

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

The composition according to the invention can also optionally comprise one or more emulsifiers the choice of which will normally determine whether a water-in-oil or oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers include but are not limited to emulsifiers set forth in Table 1 in columns 11–12 of U.S. Pat. 5,198,210 (to Critchley et al.), which is incorporated by reference herein.

It is to be understood that two or more emulsifiers can be employed if desired.

The amount of emulsifier or mixtures thereof, to be incorporated in the composition of the invention, when appropriate is from 1% to 50%, preferably from 2% to 20% and most preferably from 2% to 10% by weight of the composition.

The composition of the invention can also comprise water, usually up to 98%, preferably from 5% to 80% by volume.

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

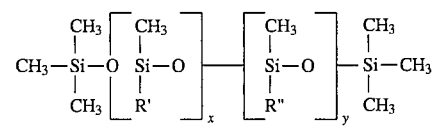

where the groups R' and R" are each chosen from —H, $C_{1-18}$ alkyl and

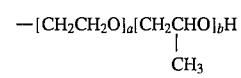

a has a value of from 9 to 115, b has a value of from 0 to 50, x has a value of from 133 to 673, y has a value of from 25 to 0.25.

Preferably, the dimethyl polysiloxane polymer is one in which:

a has a value of from 10 to 114, b has a value of from 0 to 49, x has a value of from 388 to 402, y has a value of from 15 to 0.75.

one of groups R' and R" being lauryl, and the other having a molecular weight of from 1000 to 5000.

A particularly preferred dimethyl polysiloxane polymer is one in which:

a has the value 14 b has the value 13 x has the value 249 y has the value 1.25

The dimethyl polysiloxane polymer is conveniently provided as a dispersion in a volatile siloxane, the dispersion comprising, for example, from 1 to 20% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from DOW CORNING.

The amount of silicone surfactant, when present in the composition will normally be up to 25%, preferably from 0.5 to 15% by weight of the emulsion.

Examples of other conventional cosmetic adjuncts which can optionally be employed (as long as they do not substantially reduce or eliminate the activity of transglutaminase or the active) include preservatives, such as parahydroxy benzoate esters; antioxidants, such as butyl hydroxy toluene; humectants, such as glycerol, sorbitol, 2-pyrrolidone-5-carboxylate, dibutylphthalate, gelatin, polyethylene glycol, preferably PEG 200–600; buffers, such as lactic acid together with a base such as triethanolamine or sodium hydroxide; surfactants, such as glycerol ethers and ceramides of synthetic, animal or plant origin; phospholipids; waxes, such as beeswax, ozokerite wax, paraffin wax, plant extracts, such as Aloe vera, cornflower, witch hazel, elderflower, cucumber; thickeners; activity enhancers; colorants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

Cosmetic adjuncts can form the balance of the composition.

The composition according to the invention is intended primarily as a product for topical application to human skin. The composition can also be applied to hair and nails.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The active ingredient might itself include a glutamine moiety (as may be the case when the active ingredient is a protein or a peptide). In such a case, the inventive composition must be designed to prevent transglutaminase crosslinking the active ingredient molecules prior to use. For instance, the active ingredient and transglutaminase may be placed in separate chambers in a dual chamber package, or enzyme may be placed in shear sensitive (or other induced release) capsules.

The following specific examples further illustrate the present invention but the invention is not limited thereto.

EXAMPLE 1

Transglutaminase crosslinking of [$^{14}$C]-cadaverine to isolated human corneocytes Corneocytes were harvested from seven human subjects by tape-stripping two sites on each arm, six consecutive times (with Titertek Plate Sealer Tape, ICN Biomedicals Inc., Costa Mesa, Calif.). Tapestrips from each subject were pooled in 250 ml of 2 mM SDS, 8 mM N,N-dimethyldodecylamine-N-oxide, 0.1% sodium azide, 0.1M Tris-HCl (hereinafter "Tris"), adjusted to pH 8.0, and incubated with agitation at 37° C. overnight. Tapestrips were removed in the morning and the samples were centrifuged at approximately 4500 rpm for ten minutes to pellet the corneocytes. After decanting the supernatant the corneocytes were transferred to 15 ml tubes for washing. Each batch was washed 4 times with 0.2M Tris, 5 mM calcium chloride, 0.5% Triton X-100, adjusted to pH 8.0. After the last wash, each batch was suspended in equal volumes of the same solution. Corneocyte concentrations in suspensions were determined by gravimetric methods (20 µl volumes of suspended corneocytes were dispensed into calorimetry pans, dried in a 65° C. oven, and weighed on a Perkin-Elmer AD-4 Autobalance). For each subject, 2 mg of corneocytes were dispensed in triplicate into 4 sets of 1.2 ml microfuge tubes. The four sets for each subject were treated as follows: (A) 3.4 nMoles [$^{14}$C]-Cadaverine (0.05 uCi), 0.025 units of guinea pig liver transglutaminase (Sigma Chem. Co., St. Louis, Mo.); (B) 3.4 nMoles [$^{14}$C]-Cadaverine, 0.025 units of transglutaminase, 10 mM EDTA; (C) 3.4 nMoles [$^{14}$C]-Cadaverine, and (D) 3.4 nMoles [$^{14}$C]-Cadaverine with 10 mM EDTA. Each of these treatment/reactions were run in 0.2M Tris, 5 mM calcium chloride, 40 mM glutathione (GSH), 0.5% Triton X-100, adjusted to pH 8.0 (hereafter referred to as Reaction Buffer). The addition of EDTA in controls should inhibit calcium-dependent transglutaminase thus demonstrating the difference between crosslinked and non-crosslinked cadaverine. The corneocytes in each treatment were incubated at 37° C. for four hours with shaking. After incubation the corneocytes were pelleted by centrifugation, aspirated and then washed six times with 0.2M Tris, 5 mM calcium chloride, 0.5% Triton X-100, pH 8.0, by repeated vortex agitation, centrifugation and aspiration. The washed corneocytes were then suspended in 20 ml of Scintiverse BD scintillation cocktail (Fisher Scientific, Fairlawn, N.J.) and analyzed for radioactive content on a Beckman LS 5801 scintillation counter (Beckman Instruments Inc., Irvine, Calif.) and picomoles of [$^{14}$C]-cadaverine bound was calculated.

The results that were obtained are summarized in Table 1, wherein $^{14}$C-cadaverine is abbreviated as "CAD" and transglutaminase as "TG".

TABLE 1

| TREATMENT | ($^{14}$C)-CADAVERINE BOUND (pMOLES/mg CELLS ± SD) |
|---|---|
| CAD + TG | 55.0 ± 22.7 |
| CAD + TG + EDTA | 4.7 ± 1.7 |
| CAD | 17.4 ± 12.7 |
| CAD + EDTA | 4.5 ± 1.6 |

The results in Table 1 demonstrate that significant quantities of [$^{14}$C]-cadaverine were bound to isolated human corneocytes with guinea pig liver transglutaminase. The binding was lower in the absence of enzyme and inhibitable with EDTA. Corneocytes treated with [$^{14}$C]-cadaverine and transglutaminase contained significantly more [$^{14}$C]-cadaverine than corneocytes treated with [$^{14}$C]-cadaverine, transglutaminase and EDTA (p=0.0011) or with [$^{14}$C]-cadaverine alone (p=0.0042). These data indicate that the higher degree of cadaverine binding seen in the transglutaminase containing samples was inhibited in the presence of a transglutaminase inhibitor (EDTA) and was reduced in the absence of transglutaminase. It was also observed that corneocytes treated with [$^{14}$C]-cadaverine alone incorporated significantly more radiolabel than corneocytes treated with [$^{14}$C]-cadaverine and EDTA. These results also suggest that the tape-stripped corneocytes may contain residual, endogenous transglutaminase which could be inhibited by EDTA.

EXAMPLE 1A

Corneocytes from different subjects vary in their receptivity to covalent modification by transglutaminase.

Corneocytes collected from seven different individuals (see Methods) were divided and treated, in triplicate, with (a) [$^{14}$C]-cadaverine and transglutaminase; (b) [$^{14}$C]-cadaverine, transglutaminase and EDTA; (c) [$^{14}$C]-cadaverine; or (d) [$^{14}$C]-cadaverine and EDTA. After a 4 hour incubation at 37° C., corneocytes were washed and then analyzed for radioactive content. Picomoles of [$^{14}$C]-cadaverine bound was then calculated. The results that were obtained are summarized in Table 2.

TABLE 2

| SUBJECT | ($^{14}$C)-cadaverine bound (pMoles/mg corneocytes + SD) | | | |
|---|---|---|---|---|
| | CAD/TG | CAD/TG/EDTA | CAD | CAD/EDTA |
| A | 34.1 ± 3.1 | 6.2 ± 0.6 | 10.2 ± 0.4 | 6.5 ± 0.6 |
| B | 57.9 ± 6.0 | 4.0 ± 0.4 | 13.4 ± 1.0 | 3.4 ± 0.2 |
| C | 39.3 ± 2.9 | 4.5 ± 0.2 | 8.5 ± 1.2 | 4.3 ± 0.3 |
| D | 61.8 ± 2.2 | 6.7 ± 0.3 | 16.5 ± 2.9 | 5.9 ± 0.5 |
| E | 28.2 ± 2.4 | 2.6 ± 0.2 | 8.2 ± 0.9 | 2.5 ± 0.1 |
| F | 92.1 ± 4.5 | 5.9 ± 0.3 | 44.3 ± 0.8 | 6.0 ± 0.2 |
| G | 71.4 ± 10.9 | 2.7 ± 0.1 | 20.8 ± 1.4 | 2.8 ± 0.1 |

The results in Table 2 indicate that the concentration of accessible glutamine residues in the stratum corneum may play a role in transglutaminase delivery—significant differences between individual subjects were observed, although for each subject cadaverine binding was substantially higher in the presence of transglutamine than in its absence. These differences may result from variations in available and accessible glutamines among individuals. These differences may exist for a variety of reasons; (a) There may be inherent differences in glutamine concentrations in the stratum corneum of different subjects; (b) glutamine residues may be masked to different degrees due to the presence or absence of stratum corneum lipids; or (c) The degree of surface damage due to abrasion, protein denaturation or desquamation may effect the quantity of glutamine residues available for covalent modification.

EXAMPLE 2

Transglutaminase crosslinking of [$^{14}$C]-cadaverine to isolated, intact human stratum corneum Stratum corneum was isolated from keratomed human cadaver skin samples provided by the International Institute for the Advancement of Medicine, Extort, Pa. Keratomed sheets of skin were submerged in 0.05% trypsin (in purified, distilled water) and incubated at 4° C. for up to 48 hours. The stratum corneum was then peeled away from the epidermis/dermis and rinsed thoroughly and vigorously in distilled water to remove adherent epidermal cells. After rinsing the stratum corneum was air dried on a teflon screen.

Using an epidermal biopsy punch, 8mm diameter discs were punched from the sheet of stratum corneum and weighed. In a 24-well tissue culture plate stratum corneum discs were individually treated, in triplicate sets, with either (A) 6.7 nMoles [$^{14}$C]-Cadaverine (0.1 uCi), 0.025 Units guinea pig liver transglutaminase or (B) 6.7 nMoles [$^{14}$C]-Cadaverine (0.1 uCi), 0.025 Units transglutaminase, 10 mM EDTA or (C) 6.7 nMoles [$^{14}$C]-Cadaverine (0.1 uCi) or (D) 6.7 nMoles [$^{14}$C]-Cadaverine (0.1 uCi), 10 mM EDTA. in each treatment the biopsies were suspended in 1.0 ml of reaction buffer. Stratum corneum biopsies were incubated for 4 hours at 37° C. with agitation. The wells were then aspirated and the biopsies were washed four times with 3 ml of 0.2M Tris, 5 mM calcium chloride, 0.5% Triton, adjusted to pH 8.0. The plate was agitated vigorously for each wash. After washing each biopsy was transferred to 15 ml of Scintiverse BD scintillation cocktail and analyzed for radioactive content on a Beckman LS 5801 Scintillation counter.

The results that were obtained are summarized in Table 3.

TABLE 3

| TREATMENT | ($^{14}$C)-CADAVERINE BOUND (pMOLES/mg CELLS ± SD) |
|---|---|
| CAD + TG | 12.9 ± 2.8 |
| CAD + TG + EDTA | 6.2 ± 1.6 |
| CAD | 8.6 ± 1.6 |
| CAD + EDTA | 6.1 ± 0.5 |

The results in Table 3 demonstrate that significant quantities of [$^{14}$C]-cadaverine were bound to isolated human stratum corneum with guinea pig liver transglutaminase. The binding was lower in the absence of enzyme and inhibitable with EDTA. Higher quantities of [$^{14}$C]-cadaverine were substantively bound to stratum corneum in the presence of transglutaminase than in its absence or in the presence of transglutaminase and a transglutaminase inhibitor (EDTA). In stratum corneum the amount of [$^{14}$C]-cadaverine bound in the presence of transglutaminase is lower than that in the corneocyte experiments (Example 1). This result was expected since the corneocytes in intact stratum corneum are (a) in close apposition and (b) possibly retain some of the intercellular, lamellar lipid structures. Both of these conditions may reduce the number of glutamine residues accessible for covalent modification.

EXAMPLE 3

Transglutaminase crosslinking of amine-modified, fluorescent, latex particles to human skin Keratomed human cadaver skin, obtained frozen from the International Institute for the Advancement of Medicine (Exton, Pa.) was mounted in a Milliblot Dot Blot System (Millipore Inc., Bedford, Mass.) so that discrete 6 mm diameter zones of the skin surface could be treated. Latex Fluospheres (Molecular Probes Inc., Eugene, Oreg.) of 0.2 uM diameter, with a surface modification of hexyl alkylamine groups, were suspended in reaction buffer. In quadruplicate, sets of skin surface sites were treated with either (A) Fluospheres ($3.7 \times 10^{10}$ particles, calculated amine concentration [based on the manufacturer's reported surface charge density] was approximately 0.1 mM) and 0.016 Units of transglutaminase or (B) Fluospheres, 0.016 Units of transglutaminase and 2 mM iodoacetamide in reaction buffer without GSH or (C) Fluospheres and boiled transglutaminase (0.016 Units equivalent) or (D) Fluospheres only or (E) Fluospheres and 2 mM iodoacetamide in reaction buffer without GSH (Iodoacetamide inhibits transglutaminase by binding irreversibly to a key —SH group in the active site). In each treatment volumes were adjusted to 100 ul with reaction buffer. The entire Milliblot system was incubated at 37° C. for 45 minutes. After incubation the skin was removed and washed, with agitation, with 0.2M Tris, 5 mM calcium chloride, 0.5% Triton X-100, pH 8.0 for thirty minutes with one change of solution. The skin was then washed with 1M NaCl, 0.1M Tris, 2.5 mM calcium chloride, 0.25% Triton X-100, pH 8.0 for 20 minutes and finally with the previous solution for 5 minutes. Quantities of beads retained on the skin surface after washing were determined by flourescence microspectrophotometry utilizing a PC-based, Zeiss Axiophot system. Samples with the highest fluorescence were set at 100% and all readings thereafter were normalized to this value.

The results that were obtained are summarized in Table 4:

TABLE 4

Transglutaminase-mediated crosslinking of amine-modified, fluorescent, latex particles to the surface of human skin in vitro.

| TREATMENT | FLUORESCENCE (%) |
|---|---|
| Fluospheres/TG | 100.0 |
| Fluospheres/TG/IA* | 36.3 |
| Fluospheres/Boiled TG | 39.0 |
| Fluospheres | 40.3 |
| Fluospheres/IA* | 33.5 |

*IA = iodoacetamide

The results in Table 3 indicate high [$^{14}$C]-cadaverine binding even in the absence of transglutaminase. It was hypothesized that this might be due to the highly cationic nature of cadaverine. In experiments where skin was pre-incubated with non-radioactive cadaverine, in an effort to block charged sites, background binding was still high. Also washing with 1 molar sodium chloride did not significantly remove non-covalently bound [$^{14}$C]-cadaverine in controls. Although not wishing to be bound by this theory it is believed that [$^{14}$C]-cadaverine was penetrating into the skin during the incubation periods. Accordingly, it is believed that the best results may be obtained with alkylamine containing molecules which are large enough to impede percutaneous absorption. Amine-modified Fluospheres employed in Example 3 were latex particles, 0.2 uM in diameter, containing a fluorescent dye. They were too large to penetrate into lamellar lipids in the stratum corneum and probably bulky enough to be washed off when non-enzymatically bound.

The results in Table 4 demonstrate that on skin sites incubated with Fluospheres and transglutaminase significantly more fluorescence was retained on the skin surface, after a rigorous washing protocol, than on control sites. Amine-modified, fluorescent, latex beads (0.2 um) were bound to the surface of human cadaver skin by transglutaminase. The quantity of fluorescence measured at sites where beads were incubated with transglutaminase was approximately 3–4 times higher than sites where beads were incubated without enzyme or in the presence of the transglutaminase inhibitor iodoacetamide.

Examples 1–3 demonstrate that corneocytes contain glutamine residues that could be modified by transglutaminase; further experiments with stratum corneum and human cadaver skin showed that these glutamine residues were not inaccessible due to the presence of stratum corneum lipids or corneocyte adjacency, but were available to act as amine recipients in exogenous transglutaminase-catalyzed reactions.

EXAMPLE 4

Criticality of the Presence of Amine Groups Available for Binding

Covalent delivery of detectable quantities of fluorescein isothiocyanate-bovine serum albumin (FITC-BSA) to human cadaver skin did not occur due to the lack of available lysine residues in the FITC-BSA. Since Fluorescein Isothiocyanate (FITC) crosslinks directly to amine groups few, if any, of the lysines on the native BSA should be available. Hypothetically denaturation of FITC-BSA should expose unreacted lysine residues that are protected by tertiary structure. However, an attempt to covalently bind denatured FITC-BSA to skin via transglutaminase was also unsuccessful because (1) BSA denatured by boiling, in the absence of SDS resulted in precipitation and (2) while SDS prevented precipitation, it strongly inhibited transglutaminase activity.

Example 4 demonstrates the criticality of the presence of the amine groups (available for binding) in the active compound.

EXAMPLE 5

Labelling of Extracted Hair Protein with Transglutaminase

Hair protein was extracted from the hair fiber (8M urea and 20 mM mercaptoethanol) and then impregnated into nitrocellulose paper. The treated paper was clamped into a Bio-Dot system and treated with amine modified fluorescent spheres in the presence of TGase. The treated areas of the paper exhibited significantly higher fluorescence than the controls thus indicating that extracted hair protein contains glutamine residues which are susceptible towards modification.

Labelling of Damaged Hair Fibers with Transglutaminase

Using fluorescent amines, virgin hair fibers showed little or no enhanced fluorescence over that observed with the controls following TGase treatement. However, it appears that damaged fibers display an overall significant increase in fluorescence over that observed with the controls. This is a subjective observation following the screening of a large number of single fibers and selecting and comparing the average fluorescence obtained with virgin and damaged fibers.

Example 5 demonstrates that transglutaminase can be used to effect permanent (covalent) modification of the surface of hair fibers. The process involves the covalent attachment of primary amines to exposed glutamines at the hair fiber surface. Potential benefits of such a system include permanent conditioning or damage repair where the functional group is an alkyl chain/silicone or protein respectively. Suitable silicone containing amine groups is, for instance, silicone Q2-8220™ available from DOW CORNING. Q2-8220 has a theoretical molecular weight of about 7,200 and about 2 mole % amine content.

EXAMPLE 6

This example illustrates an oil-in-water cream containing an ester of the invention.

| | % w/w |
|---|---|
| Mineral oil | 4 |
| Modified Active of Formula 9 | 0.1 |
| Transglutominase | 0.5 |
| Brij 56* | 4 |
| Alfol 16RD** | 4 |
| Triethanolamine | 0.75 |
| Butane-1,3-diol | 3 |
| Xanthan Gum | 0.3 |
| Preservative | 0.4 |
| Perfume | qs |
| Butylated hydroxy toluene | 0.01 |
| Water | to 100 |

*Brij 56 is cetyl alcohol POE (10)?
Alfol 16RD is cetyl alcohol

EXAMPLES 7–8

The following compositions according to the invention represent lotions which can be used in the treatment of dry skin:

| | % w/w | |
|---|---|---|
| | 7 | 8 |
| Modified Active of Formula 11 | 1.5 | 0.1 |
| Transglutaminase | 1.0 | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilized demineralized water | to 100 | to 100 |

EXAMPLE 9

This example illustrates an alcoholic lotion containing an amide of the invention which is suitable for application to nails.

| | % w/w |
|---|---|
| Transglutaminase | 0.5 |
| Modified Active of Formula 16 | 0.2 |
| Dimethylsulphoxide | 10 |
| Ethanol | 40 |
| Antioxidant | 0.1 |
| Perfume | qs |
| Water | to 100 |

EXAMPLES 10–11

The following compositions according to the invention represent lotions which can be used in the treatment of dry, unmanageable hair.

| | % w/w | |
|---|---|---|
| | 10 | 11 |
| Modified Active of Formula 16 | 1.5 | — |
| Modfied Active of Formula 17 | — | 0.5 |
| Transglutaminase | 0.5 | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilized demineralized water | to 100 | to 100 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A composition for topical application to human skin, hair, or nails, the composition comprising:

a) an effective amount of at least one active ingredient which includes at least one —R'NH$_2$ group and is selected from the group consisting of proteins and peptides, wherein R' is a straight aliphatic hydrocarbon chain containing from 1 to 8 carbon atoms;

b) transglutaminase in an amount effective to catalyze the crosslinking of the active ingredient to glutamine residues in human skin, hair, or nails; and c) a pharmaceutically acceptable carrier in an amount effective to deliver transglutaminase and the skin benefit ingredient to human skin, hair, or nails.

2. The composition of claim 1 wherein R' contains at least 5 carbon atoms.

3. The composition of claim 1 wherein the active ingredient is selected from the group consisting of antimicrobial compounds, UV-absorbing compounds, skin conditioning agents, hair conditioning agents, anti-inflammatory compounds, antioxidants, coloring agents, perfumes, insect repellants, and mixtures thereof.

4. The composition of claim 1 wherein the active ingredient is present in an amount of from about 0.0001% to 70% by weight of the composition.

5. The composition of claim 1 wherein transglutaminase is present in an amount of from about 0.001% to 20% by weight of the composition.

6. A method of delivering an active ingredient to human skin, hair, or nails, the method comprising applying to human skin, hair, or nails the composition of claim 1.

7. A composition for topical application to human skin, hair, or nails, the composition comprising:

a) an effective amount of at least one active ingredient which is modified to include at least one —R'NH$_2$ group attached to the active ingredient by hydrolyzable linkage as represented by formula (I)

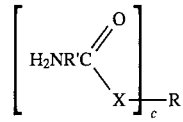

wherein R' is $(CH_2)_a(CHNH_2)_b$

X is oxygen, nitrogen, or sulphur,

R is the active ingredient part of a modified active, a is an integer from 5 to 12;

b is a number from 0 to 30, and c is a number from 1 to 4.

b) transglutaminase in an amount effective to catalyze the crosslinking of the active ingredient to glutamine residues in human skin, hair, or nails; and c) a pharmaceutically acceptable carrier in an amount effective to deliver transglutaminase and the skin benefit ingredient to human skin, hair, or nails.

8. The composition of claim 7 wherein R is an active ingredient selected from the group consisting of phenol, cresol, hydroxybenzoates, triclosan, salicylanilide, benzoates, oxybenzones, cinnamic acid, α-hydroxy acid, polyol, hyaluronic acid, corticosteroid, salicylates, ascorbates, gallates, amino acids, fats, glycinates, thymol, and vanillin.

9. A method of delivering an active ingredient to human skin, hair, or nails, the method comprising applying to human skin, hair, or nails the composition of claim 7.

* * * * *